(12) United States Patent
Yokoyama et al.

(10) Patent No.: US 10,245,584 B2
(45) Date of Patent: Apr. 2, 2019

(54) DROPLET EJECTING APPARATUS

(71) Applicant: TOSHIBA TEC KABUSHIKI KAISHA, Tokyo (JP)

(72) Inventors: Shuhei Yokoyama, Mishima Shizuoka (JP); Satoshi Kaiho, Yokohama Kanagawa (JP)

(73) Assignee: Toshiba TEC Kabushiki Kaisha, Tokyo (JP)

( * ) Notice: Subject to any disclaimer, the term of this patent is extended or adjusted under 35 U.S.C. 154(b) by 5 days.

(21) Appl. No.: 15/683,574

(22) Filed: Aug. 22, 2017

(65) Prior Publication Data

US 2018/0085745 A1 Mar. 29, 2018

(30) Foreign Application Priority Data

Sep. 23, 2016 (JP) .................................. 2016-185046

(51) Int. Cl.
| | |
|---|---|
| *B01L 3/00* | (2006.01) |
| *B01L 3/02* | (2006.01) |
| *B41J 2/055* | (2006.01) |
| *G01N 35/02* | (2006.01) |
| *G01N 35/10* | (2006.01) |

(52) U.S. Cl.
CPC .......... *B01L 3/0268* (2013.01); *B01L 3/0237* (2013.01); *B01L 3/0293* (2013.01); *B01L 3/502* (2013.01); *B41J 2/055* (2013.01); *G01N 35/02* (2013.01); *G01N 35/10* (2013.01); *G01N 35/1002* (2013.01); *G01N 35/1074* (2013.01); *B01L 2300/0829* (2013.01); *B01L 2300/0893* (2013.01); *B01L 2300/0896* (2013.01); *B01L 2300/185* (2013.01); *G01N 2035/1041* (2013.01)

(58) Field of Classification Search
CPC ......... G01N 35/10; B41J 2/145; B01L 3/0266
See application file for complete search history.

(56) References Cited

U.S. PATENT DOCUMENTS

| | | | |
|---|---|---|---|
| 6,833,112 B2* | 12/2004 | Hoummady | ......... B01J 19/0046 347/21 |
| 6,863,375 B2* | 3/2005 | Makigaki | ................... B41J 2/16 347/47 |
| 2003/0086828 A1* | 5/2003 | Chiou | ................... B01L 3/0268 422/520 |

(Continued)

OTHER PUBLICATIONS

U.S. Appl. No. 15/176,265, filed Jun. 8, 2016 (First Inventor: Ryutaro Kusunoki).

*Primary Examiner* — Jewel V Thompson
(74) *Attorney, Agent, or Firm* — Kim & Stewart LLP

(57) ABSTRACT

A droplet ejecting apparatus includes a plurality of nozzle groups each including a plurality of nozzles, a plurality of pressure chambers each configured to supply a solution to a corresponding nozzle of a nozzle group in the plurality of nozzle groups, a plurality of actuators each configured to cause a pressure change in a corresponding pressure chamber in the plurality of pressure chambers to control an ejection of a droplet of the solution from the corresponding nozzle, and a solution holding container having a solution inlet for receiving solution and a solution outlet, the solution holding container being configured to supply the solution to the plurality of nozzle groups via the plurality of pressure chambers.

20 Claims, 10 Drawing Sheets

(56) References Cited

U.S. PATENT DOCUMENTS

| | | | |
|---|---|---|---|
| 2009/0130719 A1* | 5/2009 | Handique | B01L 3/5025 |
| | | | 435/91.2 |
| 2012/0176447 A1* | 7/2012 | Otokita | B41J 2/055 |
| | | | 347/40 |
| 2014/0253640 A1 | 9/2014 | Yokoyama et al. | |
| 2018/0088142 A1* | 3/2018 | Yokoyama | G01N 35/1074 |

* cited by examiner

DROPLET EJECTING APPARATUS

CROSS-REFERENCE TO RELATED APPLICATION

This application is based upon and claims the benefit of priority from Japanese Patent Application No. 2016-185046, filed Sep. 23, 2016, the entire contents of which are incorporated herein by reference.

FIELD

Embodiments described herein relate generally to a droplet ejecting apparatus.

BACKGROUND

Fluid dispensing in a range of picoliters (pL) to microliters (μL) is often used in biological and pharmaceutical research and development, medical diagnosis and examination, or agricultural testing. For example, in studying a dose-response effect of chemotherapy, fluid dispensing with a low volume is an important task for determining the concentration of a candidate compound required to effectively attack cancer cells.

In such dose-response experiments, candidate compounds are prepared at many different concentrations in wells of a multiwell plate to determine an effective concentration. An existing on-demand type of droplet ejecting apparatus is used for the above application. For example, the droplet ejecting apparatus includes a storage container that holds a solution, a nozzle that ejects the solution supplied from the container, a pressure chamber between the container and the nozzle, and an actuator that controls pressure inside the pressure chamber to eject the solution from the nozzle.

In the droplet ejecting apparatus, the volume of one droplet ejected from an individual nozzle is on the order of a picoliter (pL). By controlling the total number of droplets ejected into each well, the droplet ejecting apparatus supplies an amount of fluid in a range of picoliters to microliters into each well. Therefore, the droplet ejecting apparatus is generally suitable for dose-response experiments when dispensing the candidate compounds at various concentrations or when dispensing in very small amounts.

A multiwell plate (also referred to as a microplate) normally used in this context has 1,536 wells (hereinafter, this multiwell plate may be referred to as a 1,536 well plate). Efforts have also been made to use a microplate having 3,456 wells (hereafter, referred to as a 3,456 well plate) and a microplate having 6,144 wells (hereinafter, referred to as a 6,144 well plate). However, in microplates having more than 1,536 wells, the wells must typically be very densely arranged. Though, it is possible to improve experimental evaluation efficiency by increasing the number of samples and to improve reagent utilization efficiency since the volume of the wells is usually smaller.

DETAILED DESCRIPTION

A droplet ejecting apparatus includes a plurality of nozzle groups each including a plurality of nozzles, a plurality of pressure chambers each configured to supply a solution to a corresponding nozzle of a nozzle group in the plurality of nozzle groups, a plurality of actuators each configured to cause a pressure change in a corresponding pressure chamber in the plurality of pressure chambers to control an ejection of a droplet of the solution from the corresponding nozzle, and a solution holding container having a solution inlet for receiving solution and a solution outlet, the solution holding container being configured to supply the solution to the plurality of nozzle groups via the plurality of pressure chambers.

Hereinafter, example embodiments will be described with reference to the drawings. Each drawing is a schematic view for illustrating the embodiments and facilitating understanding thereof. The shape, dimension, and ratio may be different from those of the actual one. Design thereof can be changed as appropriate.

One object of certain example embodiments described herein is to provide a droplet ejecting apparatus which completes a dropping task in a short time to prevent the concentration of a compound in a storage container being changed due to solution/solvent volatilization when a tested compound has been dissolved in a highly volatile solution/solvent. Over time, the solution components/solvent may evaporate or otherwise volatize from the liquid phase into the vapor phase in the storage container during the process of dropping the solution into the individual wells of 1,536/3,456/6,144 well plates.

When a microplate having many wells is used (such as the 1,536/3,456/6,144 well plates) in an on-demand type of droplet ejecting apparatus, if the solution is dropped separately into each well, it takes a long time to drop the solution into all of the wells in the microplate. Therefore, if a highly volatile solution is being dropped into the wells, there is a possibility that the solution in the storage container may be volatilized and solute concentration may be changed during the time of a dropping operation.

If the concentration of the solution changes in the storage container during the dropping operation, the concentration of the solution dropped into each well cannot be accurately recognized. Therefore, when the on-demand type of droplet ejecting apparatus carries out the task of dropping the solution in the storage container onto the microplate having many wells, for example, such as the microplate having 1,536 wells or more, the droplet ejecting apparatus preferably needs to drop the solution in the storage container into all of the wells in a short time so as to limit the solute concentration in the storage container being changed due to volatilization of solution/solvent in the storage container.

First Embodiment

Figure 1:
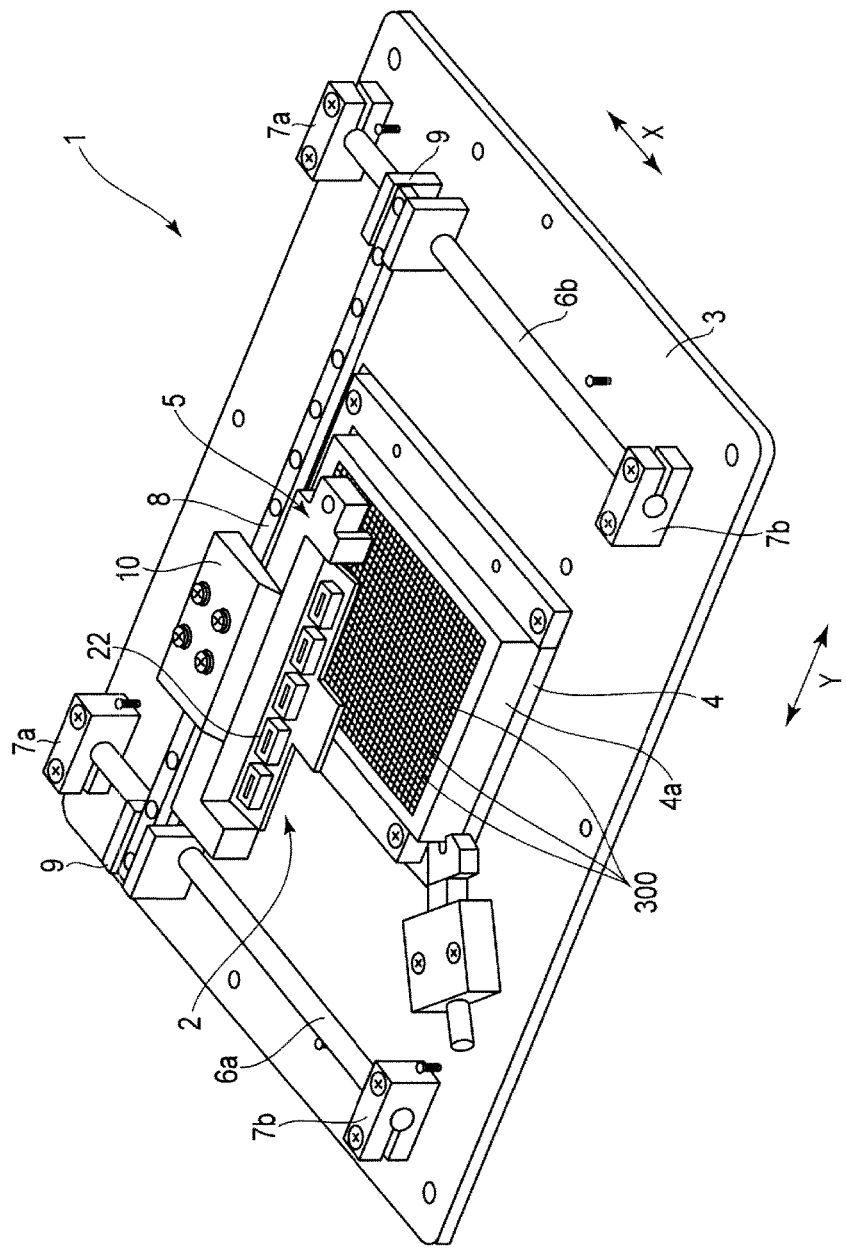
FIG. 1 is a schematic perspective view of a solution dropping apparatus equipped with a droplet ejecting apparatus according to a first embodiment.
Figure 2:
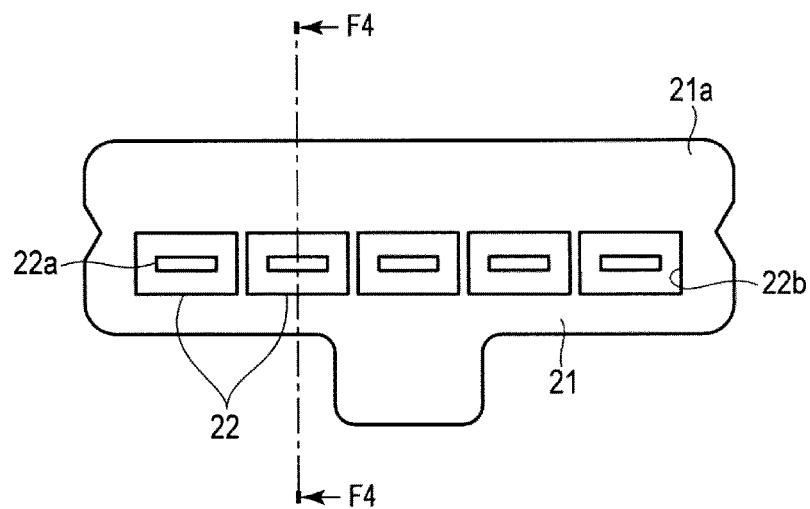
FIG. 2 is a top view of a droplet ejecting apparatus.
Figure 3:
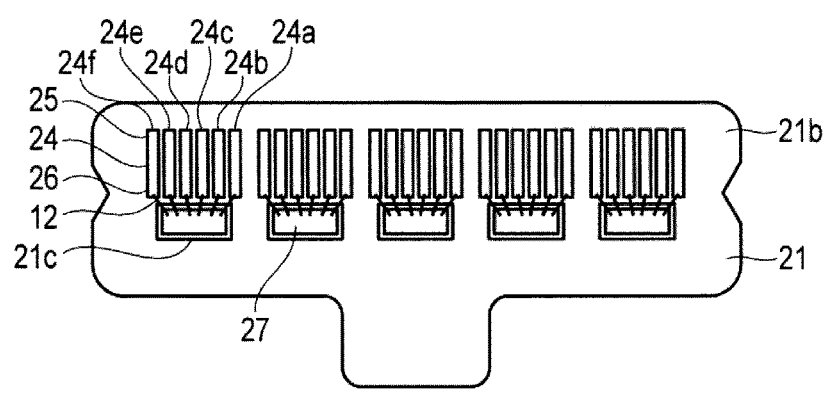
FIG. 3 is a bottom view of a droplet ejecting apparatus.
Figure 4:
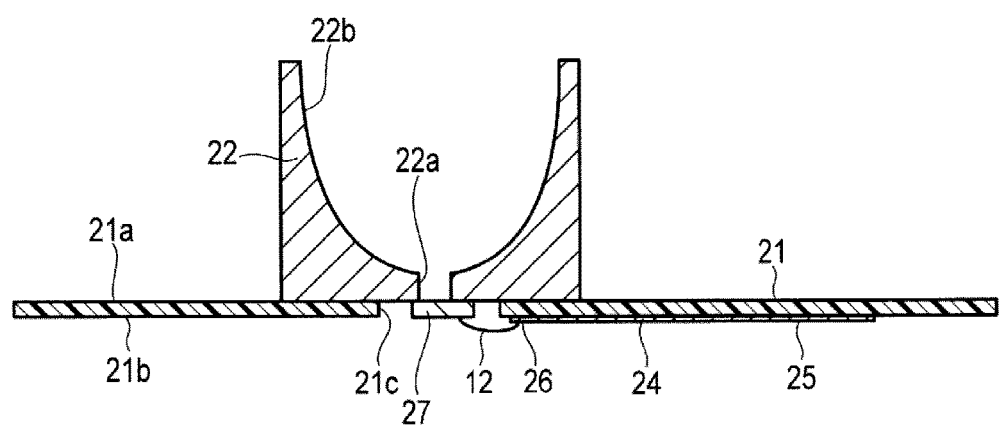
FIG. 4 is a cross-sectional view taken along line F4-F4 in FIG. 2.
Figure 5:
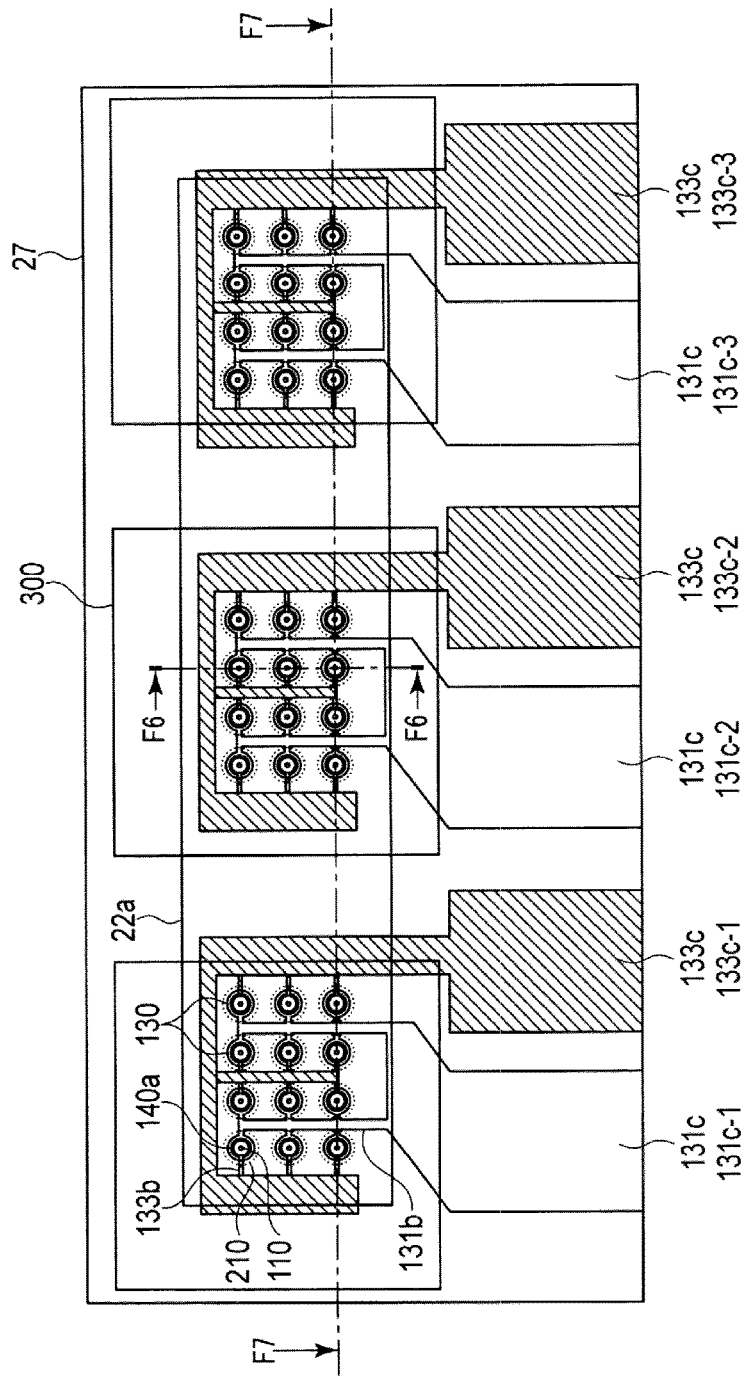
FIG. 5 is a plan view of a droplet ejecting array in a droplet ejecting apparatus.
Figure 6:
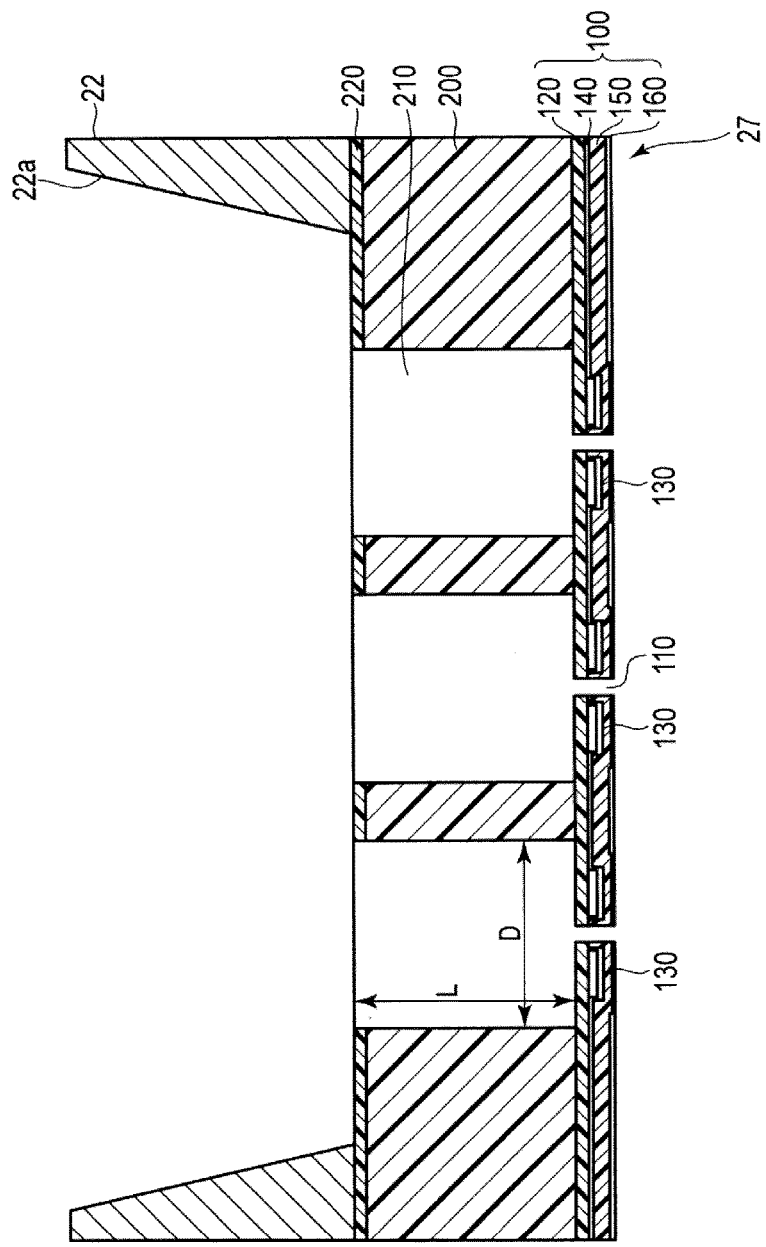
FIG. 6 is a cross-sectional view taken along line F6-F6 in FIG. 5.
Figure 7:
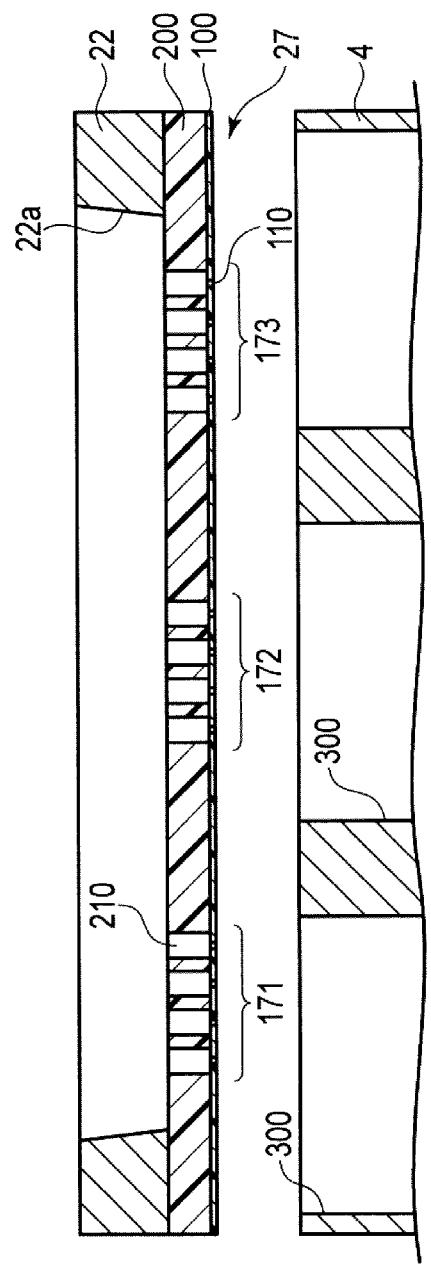
FIG. 7 is a sectional view taken along line F7-F7 in FIG. 5.
Figure 8:
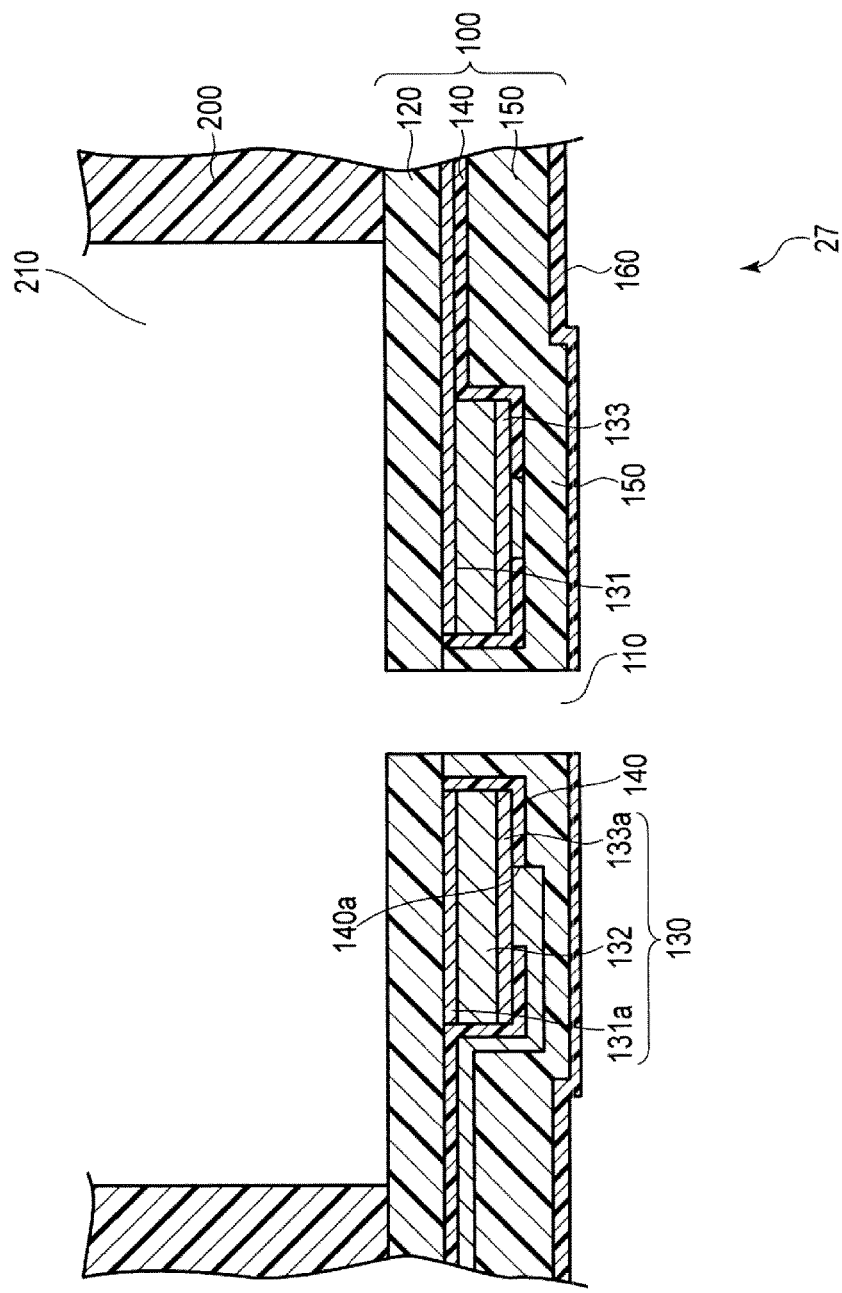
FIG. 8 is a longitudinal sectional view of a nozzle in a droplet ejecting apparatus.
Figure 9:
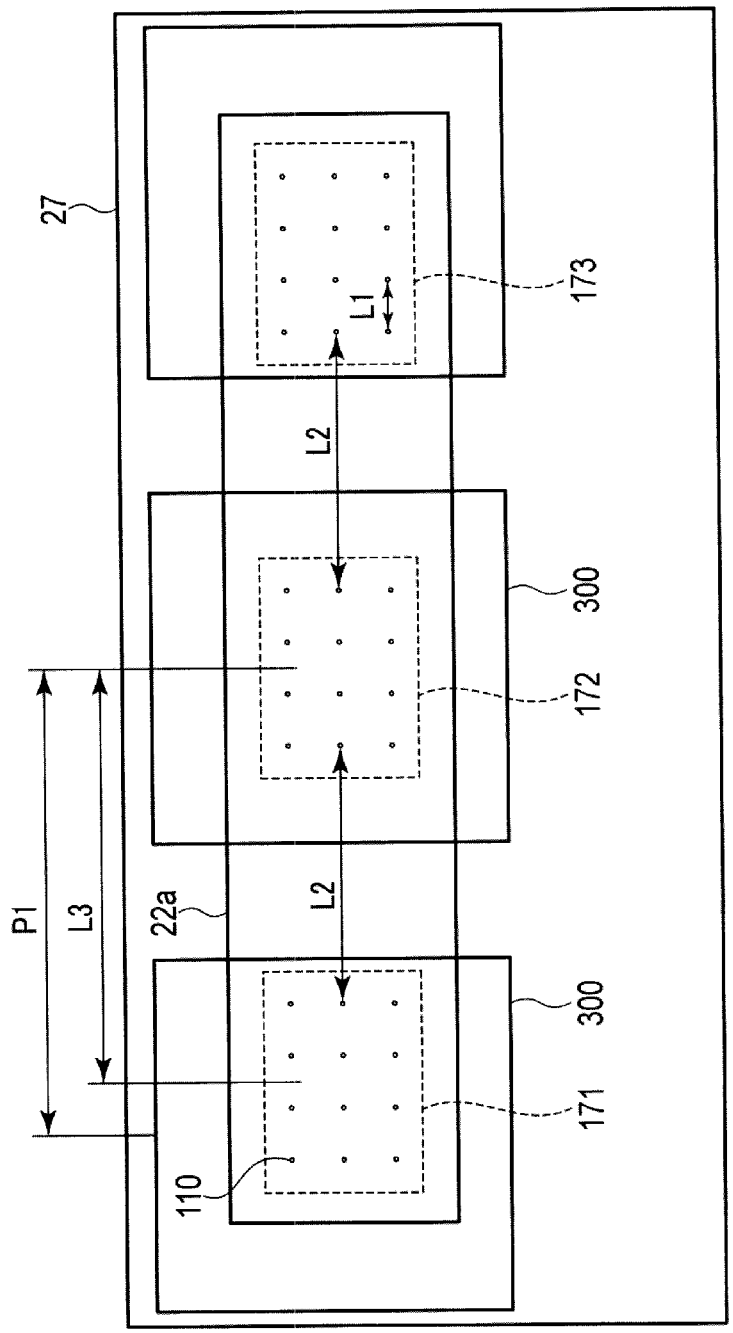
FIG. 9 is a plan view of a position relationship between a nozzle communicating with one solution holding container and a well opening of a 1,536 well microplate in a droplet ejecting apparatus.

An example of a droplet ejecting apparatus according to a first embodiment will be described with reference to FIGS. 1 to 9. FIG. 1 is a perspective view of a solution dropping apparatus 1 including a droplet ejecting apparatus 2 according to the first embodiment. FIG. 2 is a top view of the droplet ejecting apparatus 2. FIG. 3 is a bottom view of a surface where the droplet ejecting apparatus 2 ejects a droplet. FIG. 4 is a cross-sectional view taken along line F4-F4 in FIG. 2. FIG. 5 is a plan view of a droplet ejecting array 27 in the droplet ejecting apparatus 2 according to the first embodiment. FIG. 6 is a cross-sectional view taken along line F6-F6 in FIG. 5. FIG. 7 is a cross-sectional view taken along line F7-F7 in FIG. 5. FIG. 8 is a longitudinal sectional view of a nozzle 110 in the droplet ejecting apparatus 2. FIG. 9 is a plan view of a position relationship between the nozzle 110 of the droplet ejecting apparatus 2 and a well opening 300 of a 1,536 well microplate 4.

The solution dropping apparatus 1 has a rectangular plate-shaped base 3 and a droplet ejecting apparatus mounting module 5. In these examples, a solution is dropped onto the microplate 4 having 1,536 wells.

The microplate 4 is fixed to the base 3. On either side of the microplate 4 on the base 3, right and left X-direction guide rails 6a and 6b extending in an X-direction are installed. Both end portions of the respective X-direction guide rails 6a and 6b are fixed to fixing bases 7a and 7b protruding on the base 3.

A Y-direction guide rail 8 extending in a Y-direction is installed between the X-direction guide rails 6a and 6b. Both ends of the Y-direction guide rail 8 are respectively fixed to an X-direction moving table 9 which can slide in the X-direction along the X-direction guide rails 6a and 6b.

A Y-direction moving table 10 is disposed on the Y-direction guide rail 8 and can move the droplet ejecting apparatus mounting module 5 in the Y-direction along the Y-direction guide rail 8. The droplet ejecting apparatus mounting module 5 is mounted on the Y-direction moving table 10. The droplet ejecting apparatus 2 is fixed to the droplet ejecting apparatus mounting module 5. In this manner, an operation of the Y-direction moving table 10 moving in the Y-direction along the Y-direction guide rail 8 can be combined with an operation of the X-direction moving table 9 moving in the X-direction along the X-direction guide rails 6a and 6b. Accordingly, the droplet ejecting apparatus 2 is supported so as to be movable to any position in XY-directions which are orthogonal to each other.

The droplet ejecting apparatus 2 has a flat plate-shaped electrical board 21 as illustrated in FIGS. 2 and 3. As illustrated in FIG. 2, a plurality of (e.g., five in the first embodiment) rectangular box-shaped solution holding containers 22 are juxtaposed along the Y-direction on a front surface, also referred to as a first surface 21a, of the electrical board 21. As illustrated in FIG. 4, the solution holding container 22 has a bottomed and recessed shape whose upper surface is open. A rectangular lower surface opening 22a which serves as a solution outlet at the center position is formed in a bottom portion of the solution holding container 22. An opening area of an upper surface opening 22b is larger than an opening area of the lower surface opening 22a serving as the solution outlet.

As illustrated in FIG. 3, a rectangular opening 21c is formed in the electrical board 21 in each solution holding container 22. Each opening 21c is a through-hole larger than the lower surface opening 22a serving as the solution outlet of the solution holding container 22. As illustrated in FIG. 4, the lower surface opening 22a serving as the solution outlet of the solution holding container 22 is disposed so as to be located inside the opening 21c of the electrical board 21. A bottom portion of the solution holding container 22 is bonded and fixed to the first surface 21a of the electrical board 21.

An electrical board wiring 24 is patterned on a rear surface, also referred to as a second surface 21b, of the electrical board 21. Each rectangular opening 21c is connected to six wiring patterns 24a to 24f, each of the wiring patters 24a to 24f including a control signal input terminal 25, and an electrode terminal connector 26, on the electrical board wiring 24. Here, the wiring patterns 24a, 24c, and 24e are respectively connected to three terminal portions 131c, which are illustrated in FIG. 5, of a lower electrode 131. The wiring patterns 24b, 24d, and 24f are respectively connected to three terminal portions 133c, which are illustrated in FIG. 5, of an upper electrode 133.

The control signal input terminal 25 is a connector formed at one end portion of the electrical board wiring 24 for inputting a control signal from outside. The electrode terminal connector 26 is a connector formed at the other end portion of the electrical board wiring 24 for connecting the lower electrode terminal portion 131c and the upper electrode terminal portion 133c which are formed in the droplet ejecting array 27 illustrated in FIG. 5.

As illustrated in FIG. 4, the droplet ejecting array 27 is bonded and fixed onto the lower surface of the solution holding container 22, covering the lower surface opening 22a. The droplet ejecting array 27 is disposed at a position corresponding to the opening 21c of the electrical board 21.

As illustrated in FIG. 6, the droplet ejecting array 27 is formed by a stack of the nozzle plate 100 and the pressure chamber structure 200. A plurality of the nozzles 110 for ejecting the solution are arranged in the nozzle plate 100. In the first embodiment, as illustrated in FIG. 5, a plurality of the nozzles 110 are arranged in 3 rows and 4 columns in one well opening 300 of a 1,536 well microplate 4. There are three sets of 12 nozzles 110 arranged in 3 rows and 4 columns.

As illustrated in FIGS. 7 and 9, in the first embodiment, one set of 12 nozzles 110 arranged in 3 rows and 4 columns inside a well opening 300 of a 1,536 well microplate 4 is referred to as a nozzle group. That is, the droplet ejecting apparatus 2 in the first embodiment has three nozzle groups 171, 172, and 173. When the droplet ejecting array 27 is disposed above the well openings 300 of the 1,536 well microplate 4, all of the 36 nozzles 110 can be positioned above the well openings 300 of the 1,536 well microplate 4. Here, each of the three nozzle groups 171, 172, 173 is disposed inside a different one of the well openings 300.

As illustrated in FIG. 9, a pitch P1 of the well openings 300 of the 1,536 well microplate 4 is 2.25 mm. In general, the well opening 300 of the 1,536 well microplate 4 has a square shape in which each side is approximately 1.7 mm.

A center distance L1 between the adjacent nozzles 110 in the one nozzle group 173 (alternatively 171 or 172), in FIG. 9, which are arranged in 3 rows and 4 columns is 0.25 mm. Therefore, the size of one nozzle group 173 (alternatively 171 or 172) is 0.5 mm in the X-direction, and 0.75 mm in the Y-direction. The size of one nozzle group 173 (alternatively 171 or 172) is thus smaller than the size of the well opening 300 of the 1,536 well microplate 4.

A separation distance L2 between closest nozzles in adjacent nozzle groups 171, 172, and 173 is 1.25 mm. That is, the distance L2 between the closest nozzles in groups 171 and 172, or 172 and 173, respectively is longer than the distance L1 (0.25 mm) between the adjacent nozzles 110 within one nozzle group 171 (alternatively 172 or 173). Thus, each of the nozzles 110 of the droplet ejecting array 27 can be disposed inside a well opening 300 of the 1,536 well microplate 4 simultaneously.

As illustrated in FIG. 8, the nozzle plate 100 includes a drive element 130 serving as a drive unit, a protective film 150 serving as a protective layer, and a fluid repellent film 160, on a diaphragm 120. The actuator corresponds to the diaphragm 120 and the drive element 130. In some embodiments, the diaphragm 120 may be integrated with the pressure chamber structure 200. For example, when the chamber structure 200 is manufactured on a silicon wafer 201 by a heat treatment in an oxygen atmosphere, a $SiO_2$ (silicon oxide) film is formed on a surface of the silicon wafer 201. The diaphragm 120 may be the $SiO_2$ (silicon oxide) film on the surface of the silicon wafer 201 formed through the heat treatment in the oxygen atmosphere. The diaphragm 120 may be formed using a chemical vapor deposition (CVD) method by depositing the $SiO_2$ (silicon oxide) film on the surface of the silicon wafer 201.

It is preferable that the film thickness of the diaphragm 120 is within a range of 1 to 30 μm. The diaphragm 120 may be of a semiconductor material such as a SiN (silicon nitride) or $Al_2O_3$ (aluminum oxide).

The drive element 130 is formed for each of the nozzles 110. The drive element 130 has an annular shape surrounding the nozzle 110. A shape of the drive element 130 is not limited, and may be a C-shape obtained by partially cutting the annular shape, for example. As illustrated in FIG. 8, the drive element 130 includes an electrode portion 131a of the lower electrode 131 and an electrode portion 133a of the upper electrode 133, interposing a piezoelectric film 132 serving as a piezoelectric body. The electrode portion 131a, the piezoelectric film 132, and the electrode portion 133a are circular coaxial with the nozzle 110 and have similar diameters.

The lower electrode 131 includes a plurality of circular electrode portions 131a each coaxial with a corresponding circular nozzle 110. For example, the nozzle 110 may have a diameter of 20 μm, and the electrode portion 131a may have an outer diameter of 133 μm and an inner diameter of 42 μm. As illustrated in FIG. 5, the lower electrode 131 includes a wiring portion 131b which connects the plurality of electrode portions 131a to one another. An end portion of the wiring portion 131b includes a terminal portion 131c. In the drive element 130 as illustrated in FIG. 5, the electrode portion 131a of the lower electrode 131 and the electrode portion 133a of the upper electrode 133 are overlaid.

The drive element 130 includes the piezoelectric film 132 formed of a piezoelectric material having the thickness of 2 μm, for example, on the electrode portion 131a of the lower electrode 131. The piezoelectric film 132 may be formed of PZT (Pb(Zr, Ti) $O_3$: lead titanate zirconate). For example, the piezoelectric film 132 is coaxial with the nozzle 110, and has an annular shape whose outer diameter is 133 μm and inner diameter is 42 μm, which is the same shape as the shape of the electrode portion 131a. The film thickness of the piezoelectric film 132 is set to a range of approximately 1 to 30 μm. For example, the piezoelectric film 132 may be of a piezoelectric material such as PTO ($PbTiO_3$: lead titanate), PMNT ($Pb(Mg_{1/3}Nb_{2/3})\ O_3$—$PbTiO_3$), PZNT ($Pb(Zn_{1/3}Nb_{2/3})\ O_3$—$PbTiO_3$), ZnO, and AlN.

The piezoelectric film 132 generates polarization in a direction parallel to a thickness of the piezoelectric film 132. If an electric field in the direction of the polarization is applied to the piezoelectric film 132, the piezoelectric film 132 expands and contracts in a direction orthogonal to the electric field. In other words, the piezoelectric film 132 contracts or expands in a direction orthogonal to the film thickness.

The upper electrode 133 of the drive element 130 is coaxial with the nozzle 110 on the piezoelectric film 132, and has an annular shape whose outer diameter is 133 μm and inner diameter is 42 μm, which is the same shape as the shape of the piezoelectric film 132. As illustrated in FIG. 5, the upper electrode 133 includes a wiring portion 133b which connects the plurality of the electrode portions 133a to one another. An end portion of the wiring portion 133b includes a terminal portion 133c. If a predetermined voltage is applied to the upper electrode 133, a voltage control signal is applied to the lower electrode 131.

For example, the lower electrode 131 may be formed with a thickness of 0.5 μm by stacking Ti (titanium) and Pt (platinum) using a sputtering method. The film thickness of the lower electrode 131 is in a range of approximately 0.01 to 1 μm. The lower electrode 131 may be of other materials such as Ni (nickel), Cu (copper), Al (aluminum), Ti (titanium), W (tungsten), Mo (molybdenum), Au (gold), and $SrRuO_3$ (strontium rutheniumoxide). The lower electrode 131 may also be of various stacked metal materials.

The upper electrode 133 is formed of a Pt thin film. The thin film is formed using a sputtering method, and the film thickness is set to 0.5 μm. As other electrode materials of the upper electrode 133, Ni, Cu, Al, Ti, W, Mo, Au, and $SrRuO_3$ can be used. As another film formation method, vapor deposition and plating can be used. The upper electrode 133 may be of various stacked metal materials. The desirable film thickness of the upper electrode 133 is 0.01 to 1 μm.

The nozzle plate 100 includes the insulating film 140 which insulates the lower electrode 131 and the upper electrode 133 from each other. For example, $SiO_2$ (silicon oxide) having the thickness of 0.5 μm is used for the insulating film 140. In a region proximate to the drive element 130, the insulating film 140 covers the periphery of the electrode portion 131a, the piezoelectric film 132, and the electrode portion 133a. The insulating film 140 covers the wiring portion 131b of the lower electrode 131. The insulating film 140 covers the diaphragm 120 in the region proximate to the wiring portion 133b of the upper electrode 133. The insulating film 140 includes a contact portion 140a which electrically connects the electrode portion 133a and the wiring portion 133b of the upper electrode 133 to each other.

The nozzle plate 100 includes the protective film 150 formed of polyimide, for example, which protects the drive element 130. The protective film 150 includes a cylindrical solution passage 141 communicating with the nozzle 110 in the diaphragm 120. The solution passage 141 has the diameter of 20 μm which is the same as the diameter of the nozzle 110 in the diaphragm 120.

The protective film 150 may be of other insulating materials such as other resins or ceramics. Examples of other resins include ABS (acrylonitrile butadiene styrene), polyacetal, polyamide, polycarbonate, and polyether sulfone. For example, ceramics include zirconia, silicon carbide, silicon nitride, and silicon oxide. The film thickness of the protective film 150 is in a range of approximately 0.5 to 50 µm.

For selecting the material for the protective film 150, the following factors are considered such as the Young's modulus, heat resistance, insulation quality, which determines influence of solution deterioration due to contact with the upper electrode 133 when the drive element 130 is driven in a state of using a highly conductive solution, the coefficient of thermal expansion, smoothness, and wettability to solution.

The nozzle plate 100 includes a fluid repellent film 160 which covers the protective film 150. The fluid repellent film 160 is formed, for example, by spin-coating a silicone resin so as to have a property of repelling a solution. The fluid repellent film 160 can be formed of a material such as a fluorine-containing resin. The thickness of the fluid repellent film 160 is in a range of approximately 0.5 to 5 µm.

The pressure chamber structure 200 is formed using silicon wafer 201 having the thickness of 525 µm, for example. The pressure chamber structure 200 includes a warp reduction film 220 serving as a warp reduction layer on a surface opposite to the diaphragm 120. The pressure chamber structure 200 includes a pressure chamber 210 which penetrates the warp reduction film 220, reaches a position of the diaphragm 120, and communicates with the nozzle 110. The pressure chamber 210 is formed in a circular shape having the diameter of 190 µm which is located coaxially with the nozzle 110, for example. The shape and size of the pressure chamber 210 are not limited.

However, in the first embodiment, the pressure chamber 210 includes an opening which communicates with the lower surface opening 22a of the solution holding container 22. It is preferable that a size L in a depth direction of the pressure chamber is larger than a size D in a width direction of the opening of the pressure chamber 210. Accordingly, due to the oscillation of the diaphragm 120 of the nozzle plate 100, the pressure applied to the solution contained in the pressure chamber 210 is delayed in escaping to the solution holding container 22.

A side on which the diaphragm 120 of the pressure chamber 210 is disposed is referred to as a first surface of the pressure chamber structure 200, and a side on which the warp reduction film 220 is disposed is referred a second surface of the pressure chamber structure 200. The solution holding container 22 is bonded to the warp reduction film 220 side of the pressure chamber structure 200 by using an epoxy adhesive, for example. The pressure chamber 210 of the pressure chamber structure 200 communicates with the lower surface opening 22a of the solution holding container 22 through the opening on the warp reduction film 220 side. An opening area of the lower surface opening 22a of the solution holding container 22 is larger than a total area of openings of the pressure chambers 210 in the droplet ejecting array 27 connecting to the lower surface opening 22a of the solution holding container 22. Therefore, all of the pressure chambers 210 communicating with the nozzle groups 171, 172, and 173 formed in the droplet ejecting array 27 communicate with the lower surface opening 22a of the solution holding container 22.

For example, the warp reduction film 220 is formed in such a way that the silicon wafer 201 is subjected to heat treatment in an oxygen atmosphere, and employs the $SiO_2$ (silicon oxide) film (having a thickness of 4 µm) which is formed on the surface of the silicon wafer 201. The warp reduction film 220 may also be formed by depositing a $SiO_2$ (silicon oxide) film on the surface of the silicon wafer 201 using a chemical vapor deposition method (CVD method). The warp reduction film 220 reduces warp occurring in the droplet ejecting array 27.

The warp reduction film 220 is on the side opposite to the side where the diaphragm 120 is formed on the silicon wafer 201. The warp reduction film 220 reduces the warp of the silicon wafer 201 which is caused by a difference in film stress between the pressure chamber structure 200 and the diaphragm 120 and further a difference in film stress between various configuration films of the drive element 130. The warp reduction film 220 reduces the warp of the droplet ejecting array 27 if the droplet ejecting array 27 is prepared using a deposition process.

The material and the film thickness of the warp reduction film 220 may be different from those of the diaphragm 120. However, if the warp reduction film 220 employs the material and the film thickness which are the same as those of the diaphragm 120, the difference in the film stress between the diaphragms 120 on both sides of the silicon wafer 201 is the same as the difference in the film stress between the warp reduction films 220. If the warp reduction film 220 employs the material and the film thickness which are the same as those of the diaphragm 120, the warp occurring in the droplet ejecting array 27 may be more effectively reduced.

The diaphragm 120 is deformed in the thickness direction by the operation of the drive element 130 having a planar shape. The droplet ejecting apparatus 2 ejects the solution supplied to the nozzle 110 due to a pressure change in the pressure chamber 210 of the pressure chamber structure 200 which is caused by the deformation of the diaphragm 120.

An example of a manufacturing method of the droplet ejecting array 27 will be described. In the droplet ejecting array 27, the $SiO_2$ (silicon oxide) film is first formed on both entire surfaces of the silicon wafer 201 for forming the pressure chamber structure 200. The $SiO_2$ (silicon oxide) film formed on one surface of the silicon wafer 201 is used as the diaphragm 120. The $SiO_2$ (silicon oxide) film formed on the other surface of the silicon wafer 201 is used as the warp reduction film 220.

For example, the $SiO_2$ (silicon oxide) films are formed on both surfaces of the disc-shaped silicon wafer 201 using a thermal oxidation method in which heat treatment is performed in an oxygen atmosphere using a batch type reaction furnace. Next, the plurality of nozzle plates 100 and pressure chambers 210 are formed on the disc-shaped silicon wafer 201 using a deposition process. After the nozzle plate 100 and the pressure chamber 210 are formed, the disc-shaped silicon wafer 201 is cut and separated into the plurality of pressure chamber structures 200 integrated with the nozzle plate 100. The plurality of droplet ejecting arrays 27 can be mass-produced at once using the disc-shaped circular silicon wafer 201. The silicon wafer 201 may not have a disc shape. A rectangular silicon wafer 201 may be used so as to separately form the nozzle plate 100 and the pressure chamber structure 200 which are integrated with each other.

The diaphragm 120 formed on the silicon wafer 201 is patterned using an etching mask so as to form the nozzle 110. The patterning may use a photosensitive resist as a material of the etching mask. After the photosensitive resist is coated on the surface of the diaphragm 120, exposure and development are performed to form the etching mask in which the opening corresponding to the nozzle 110 is patterned. The diaphragm 120 is subjected to dry etching from above the etching mask until the dry etching reaches the pressure chamber structure 200 so as to form the nozzle 110. After the nozzle 110 is formed in the diaphragm, the etching mask is removed using a stripping solution, for example.

Next, the drive element 130, the insulating film 140, the protective film 150, and the fluid repellent film 160 are formed on the surface of the diaphragm 120 having the nozzle 110 formed thereon. In forming the drive element 130, the insulating film 140, the protective film 150, and the fluid repellent film 160, a film forming process and a patterning process are repeatedly performed. The film forming process is performed using a sputtering method, a CVD method, or a spin coating method. For example, the patterning is performed in such a way that the etching mask is formed on the film using the photosensitive resist and the etching mask is removed after the film material is etched.

The materials of the lower electrode 131, the piezoelectric film 132, and the upper electrode 133 are stacked on the diaphragm 120 so as to form a film. As the material of the lower electrode 131, a Ti (titanium) film and a Pt (platinum) film are sequentially formed using a sputtering method. The Ti (titanium) and Pt (platinum) films may be formed using a vapor deposition method or by means of plating.

As the material of the piezoelectric film 132, PZT (Pb(Zr, Ti) $O_3$: lead titanate zirconate) is deposited on the lower electrode 131 using an RF magnetron sputtering method at the board temperature of 350° C. When the PZT film is subjected to heat treatment at 500° C. for 3 hours after the PZT film is formed, the PZT film can obtain satisfactory piezoelectric performance. The PZT film may be formed using a chemical vapor deposition (CVD) method, a sol-gel method, an aerosol deposition (AD) method, or a hydrothermal synthesis method.

As the material of the upper electrode 133, the Pt (platinum) film may be deposited on the piezoelectric film 132 using the sputtering method. On the deposited Pt (platinum) film, an etching mask is prepared to leave the lower electrode 131 and the electrode portion 133a of the upper electrode 133 and the piezoelectric film 132. The Pt (platinum) and PZT (Pb(Zr, Ti) $O_3$: lead titanate zirconate) films are removed by etching from above the etching mask, thereby forming the electrode portion 133a of the upper electrode 133 and the piezoelectric film 132.

Next, the etching mask which leaves the electrode portion 131a of the lower electrode 131, the wiring portion 131b, and the terminal portion 131c is formed on the lower electrode 131 on which the electrode portion 133a of the upper electrode and the piezoelectric film 132 are formed. Etching is performed from above the etching mask, and the Ti (titanium) and Pt (platinum) films are removed so as to form the lower electrode 131.

As the material of the insulating film 140, the $SiO_2$ (silicon oxide) film is formed on the diaphragm 120 on which the lower electrode 131, the electrode portion 133a of the upper electrode, and the piezoelectric film 132 are formed. For example, the $SiO_2$ (silicon oxide) film may be formed at low temperature using the CVD method so as to obtain satisfactory insulating performance. The formed $SiO_2$ (silicon oxide) film is patterned so as to form the insulating film 140.

As the material of the wiring portion 133b and the terminal portion 133c of the upper electrode 133, Au (gold) is deposited using the sputtering method on the diaphragm 120 having the insulating film 140 formed thereon. The Au (gold) film may be formed using the vapor deposition method or the CVD method, or by means of plating. The etching mask which leaves the electrode wiring portion 133b and the terminal portion 133c of the upper electrode 133 is formed on the deposited Au (gold) film. Etching is performed from above the etching mask, the Au (gold) film is removed so as to form the electrode wiring portion 133b and the terminal portion 133c of the upper electrode 133.

A polyimide film, which may be the material of the protective film 150, is formed on the diaphragm 120 having the upper electrode 133 formed thereon. The polyimide film is formed in such a way that a solution containing a polyimide precursor is coated on the diaphragm 120 using a spin coating method and thermal polymerization is performed by means of baking so as to remove a solvent. The formedpolyimide film is patterned so as to form the protective film 150 which exposes the solution passage 141, the terminal portion 131c of the lower electrode 131, and the terminal portion 133c of the upper electrode 133.

A silicone resin film, which may be the material of the fluid repellent film 160, is coated on the protective film 150 using a spin coating method, and thermal curing is performed by means of baking so as to remove the solvent. The formed silicone resin film is then patterned so as to form the fluid repellent film 160 which exposes the nozzle 110, the solution passage 141, the terminal portion 131c of the lower electrode 131, and the terminal portion 133c of the upper electrode 133.

For example, a rear surface protective tape for chemical mechanical polishing (CMP) of the silicon wafer 201 may adhere onto the fluid repellent film 160 as a cover tape so as to protect the fluid repellent film 160 and the pressure chamber structure 200 can be patterned. The etching mask which exposes the pressure chamber 210 with the diameter of 190 µm is formed on the warp reduction film 220 of the silicon wafer 201. First, the warp reduction film 220 is subjected to dry etching using mixed gas of $CF_4$ (carbon tetrafluoride) and $O_2$ (oxygen). Next, for example, vertical deep dry etching preferentially for the silicon wafer is performed using mixed gas of $SF_6$ (sulfur hexafluoride) and $O_2$. The dry etching is stopped at a position in contact with the diaphragm 120, thereby forming the pressure chamber 210 in the pressure chamber structure 200.

The etching for forming the pressure chamber 210 may be performed by a wet etching method using a liquid etchant or a dry etching method using plasma. After the etching is completed, the etching mask is removed. A cover tape adhering onto the fluid repellent film 160 is irradiated with ultraviolet light so as to weaken adhesiveness therebetween, and the cover tape is detached from the fluid repellent film 160. The disc-shaped silicon wafer 201 is diced so as to separately form the plurality of droplet ejecting arrays 27.

Next, a manufacturing method of the droplet ejecting apparatus 2 will be described. The droplet ejecting array 27 and the solution holding container 22 are bonded to each other. In this case, a bottom surface, on the same side as the opening 22a, of the solution holding container 22 is bonded to the warp reduction film 220 of the pressure chamber structure 200 in the droplet ejecting array 27.

Thus, the solution holding container 22 bonded to the droplet ejecting array 27 is bonded to the first surface 21a of the electrical board 21 so that the opening 22a of the solution holding container 22 fits inside the opening 21c of the electrical board 21.

Subsequently, the electrode terminal connector 26 and the terminal portion 131c of the lower electrode 131 and the terminal portion 133c of the upper electrode 133 of the droplet ejecting array 27 are connected to each other by wiring 12. A connection method may be using a flexible cable. An electrode pad of the flexible cable can be electrically connected to the electrode terminal connector 26. The terminal portion 131c and the terminal portion 133c may be electrically connected via an anisotropic conductive film formed by thermocompression bonding.

The control signal input terminal 25 on the electrical board wiring 24 has a shape which can come into contact with a leaf spring connector for inputting a control signal that is output from a control circuit (not illustrated), for example. This forms the droplet ejecting apparatus 2.

FIG. 9 is an enlarged plan view of the bottom portion of the solution holding container 22, including the nozzle 110 and the opening 22a, and the well opening 300 of the 1,536 well microplate 4, illustrated in FIG. 5. The terminal portion 131c and the terminal portion 133c which are connected to the drive element 130 for ejecting the solution from the nozzle group 171 are respectively referred to as a terminal portion 131c-1 and a terminal portion 133c-1. Similarly, the terminal portion 131c and the terminal portion 133c which are connected to the drive element 130 for ejecting the solution from the nozzle groups 172 and 173 are respectively referred to as a terminal portion 131c-2 and a terminal portion 133c-2, and a terminal portion 131c-3 and a terminal portion 133c-3.

In this case, the wiring patterns 24a and 24b of the electrical board wiring 24 in FIG. 3 are connected to the terminal portion 131c-1 and the terminal portion 133c-1 of the nozzle group 171. The wiring patterns 24c and 24d on the electrical board wiring are connected to the terminal portion 131c-2 and the terminal portion 133c-2 of the nozzle group 172, and the wiring patterns 24e and 24f of the electrical board wiring are connected to the terminal portion 131c-3 and the terminal portion 133c-3 of the nozzle group 173.

Next, an operation of the above-described configuration will be described. The droplet ejecting apparatus 2 is fixed to the droplet ejecting apparatus mounting module 5 of the solution dropping apparatus 1. When the droplet ejecting apparatus 2 is used, a predetermined amount of the solution is first supplied to the solution holding container 22 from the upper surface opening 22b of the solution holding container 22 by a pipette (not illustrated) or the like. The solution is held within the solution holding container 22. The opening 22a at the bottom portion of the solution holding container 22 communicates with the droplet ejecting array 27. Each pressure chamber 210 of the droplet ejecting array 27 is supplied with the solution from the solution holding container 22 via the opening 22a at the bottom surface of the solution holding container 22.

Next, the droplet ejecting apparatus mounting module 5 moves so that the nozzle groups 171, 172, and 173 are respectively positioned directly above the interiors of three different well openings 300 of the 1,536 well microplate 4.

In this position, a voltage control signal input to the control signal input terminal 25 is transmitted from the electrode terminal connector 26 to the terminal portion 131c of the lower electrode 131 and the terminal portion 133c of the upper electrode 133. At this time, in response to the voltage control signal applied to the drive element 130, the diaphragm 120 is deformed so as to change the volume of the pressure chamber 210. In this manner, the solution in the nozzle 110 of the droplet ejecting array 27 is ejected as a solution droplet. A predetermined amount of solution is dropped from the nozzle 110 into the three well openings 300 of the microplate 4.

The amount of one droplet ejected from the nozzle 110 is in a range of 2 to 5 picoliters. Therefore, the amount of solution ejected into each well opening 300 can be controlled on the order of pL to μL by controlling the number of ejected droplets.

In the droplet ejecting apparatus 2 according to the first embodiment, one solution holding container 22 communicates with the three nozzle groups 171, 172, and 173, and the three nozzle groups 171, 172, and 173 are respectively located immediately above the interior of the three different well openings 300 of the 1,536 well microplate 4. Accordingly, the solution can be simultaneously dropped into the three well openings 300. Therefore, when the solution of the solution holding container 22 is to be dropped into each well of the 1,536 well microplate 4, the dropping time can be shortened to ⅓ compared to the droplet ejecting apparatus in which one solution holding container 22 communicates with only one nozzle group. As a result, even a compound dissolved in a highly volatile solution can be dropped into the 1,536 well microplate 4 in a short period of time. Therefore, it is possible to provide the droplet ejecting apparatus in which the concentration of the compound is less changed by the volatilization of the solution contained in the solution holding container.

A center-to-center distance L3 between the adjacent nozzle groups 171 and 172 or between the nozzle groups 172 and 173 is 2 mm. This distance L3 is shorter than the pitch P1 (2.25 mm) of the well openings 300 of the 1,536 well microplate 4. Therefore, the size of the droplet ejecting array 27 is smaller than when the centers of the nozzle groups 171, 172, and 173 are each positioned to be directly above the center of a well opening 300 of the 1,536 well microplate 4. As a result, the number of the droplet ejecting arrays 27 which can be formed in the silicon wafer 201 can be increased. Therefore, the production cost of the droplet ejecting apparatus 2 can be reduced.

In the droplet ejecting apparatus 2 according to the first embodiment, the solution holding container 22 communicates with a plurality of the nozzle groups 171, 172, and 173. Accordingly, the solution can be simultaneously dropped into a corresponding plurality of the well openings 300 of the 1,536 well microplate 4. Therefore, the solution can be dropped into every well of a 1,536 well microplate 4 in a short period of time. Therefore, it is possible to provide the droplet ejecting apparatus 2 which limits the effect of the volatilization of the solution held in the solution holding container 22.

Second Embodiment

Figure 10:
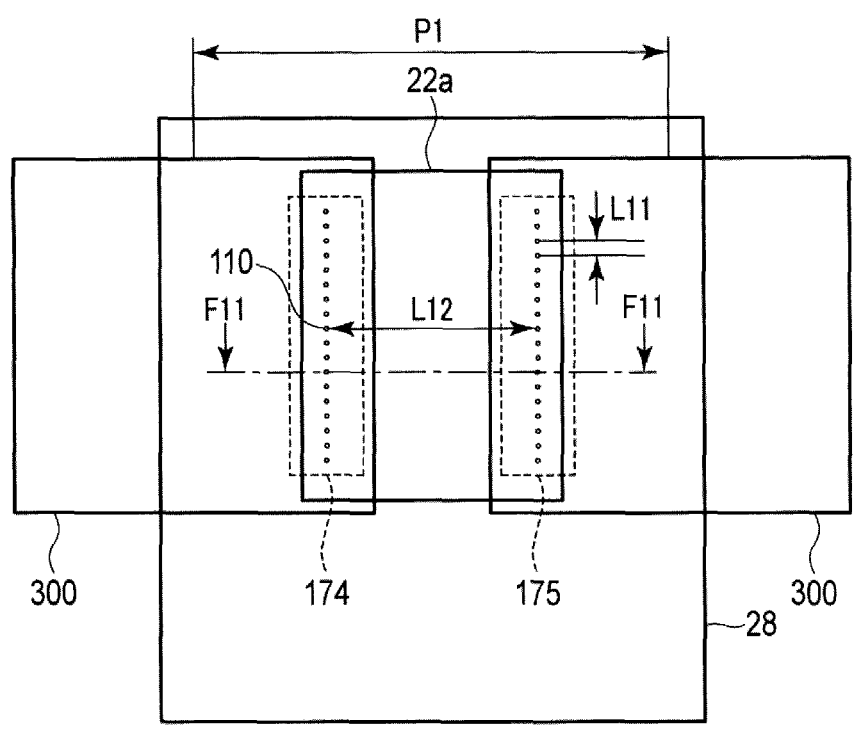
FIG. 10 is a plan of a position relationship between a nozzle communicating with one solution holding container and a well opening of a 1,536 well microplate in a droplet ejecting apparatus according to a second embodiment.
Figure 11:
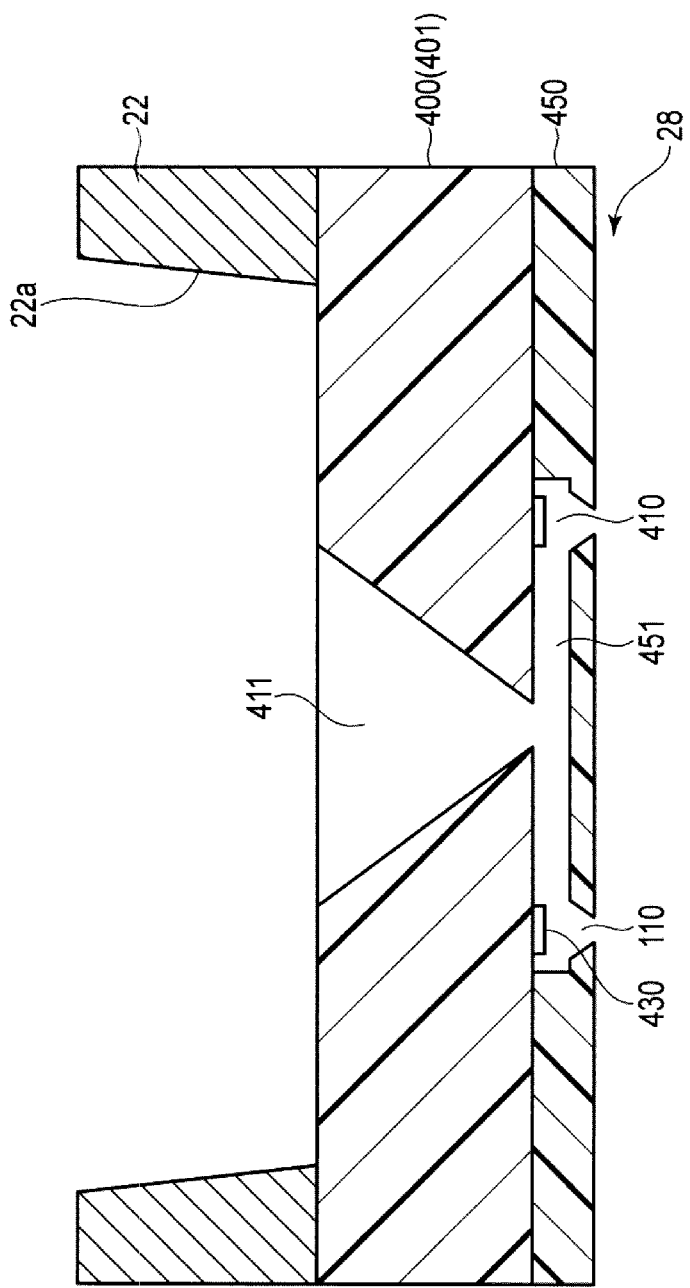
FIG. 11 is a cross-sectional view taken along line F11-F11 in FIG. 10.

FIGS. 10 and 11 illustrate a droplet ejecting apparatus 2 according to a second embodiment. The second embodiment is a modification example in which the configuration of the droplet ejecting apparatus 2 according to the first embodiment, as illustrated in FIGS. 1 to 9, is modified as follows. In the first embodiment, a piezoelectric jet method has been described as an example in which the drive element 130 serving as a portion of the actuator is a piezoelectric element, and in which the solution is ejected by the deformation of the drive element 130. In the second embodiment, an actuator uses a thermal jet method.

FIG. 10 is a plan view of a position relationship between the nozzle 110 of the droplet ejecting apparatus 2 and the well opening 300 of the 1,536 well microplate 4. FIG. 11 is a sectional view taken along line F10-F10 in FIG. 10. The same reference numerals are used for the components that are substantially the same as those of the first embodiment, and the description repeated components may be omitted.

As illustrated in FIG. 11, the droplet ejecting array 28 according to the second embodiment is formed by a stack of a silicon board 400 and a photosensitive resin film 450. A front surface side, also referred to as a second surface 400a, of the silicon board 400 has an inlet 411 communicating with the lower surface opening 22a serving as the solution outlet of the solution holding container 22. A rear surface side, also referred to as first surface 400b, of the silicon board 400 has a thin film heater 430 serving as an actuator, and wires (not illustrated) connected to the thin film heater 430.

The photosensitive resin film 450 corresponds to the board having a pressure chamber 410 formed thereon. The photosensitive resin film 450 has a flow path 451 communicating with the inlet 411, the pressure chamber 410, and the nozzle 110. The pressure chamber 410 is a region where the thin film heater 430 is disposed in the flow path 451. The solution contained in the pressure chamber 410 is heated and boiled by thermal energy generated from the thin film heater 430, thereby being ejected from the nozzle 110.

As illustrated in FIG. 10, the droplet ejecting array 28 has two rows of nozzles corresponding to the nozzle groups 174 and 175. Each of the nozzle groups 174 and 175 is obtained by respectively arranging 18 nozzles 110 in one row. The droplet ejecting array 28 formed such that each of the 36 nozzles 11 is inside a well opening 300 of the 1,536 well microplate 4, when the droplet ejecting array 28 is directly above the 1,536 well microplate 4. Therefore, each of the 36 nozzles 110 of the droplet ejecting array 28 can be disposed inside a well opening 300 of the 1,536 well microplate 4 simultaneously.

A center distance L11 between the adjacent nozzles 110 in each nozzle group 174 or 175 that are arrayed in one row is 0.07 mm. Therefore, the size of one nozzle group 174 or 175 in the nozzle array direction is 1.19 mm in the X-direction. The size of each nozzle group 174 or 175 is thus smaller than the size (1.7 mm) of the well opening 300 of a 1,536 well microplate 4.

A distance L12 between the closest nozzles 110 in adjacent nozzle groups 174 and 175 is 1 mm. The distance L12 of the closest nozzles 110 between the nozzle groups 174 and 175 is thus longer than the distance L11 (0.07 mm) between the adjacent nozzles 110 within each nozzle group.

Next, an example of a manufacturing method of the droplet ejecting array 28 according to the second embodiment described herein will be described. The droplet ejecting array 28 is formed on one side surface, also referred to as the first surface 400b, of the silicon wafer 401 in such a way that a film forming process and a patterning process are repeatedly performed on the thin film heater 430 and wires (not illustrated) are connected to the thin film heater 430. A surface having the thin film heater 430 of the silicon wafer 401 and the wires formed thereon is referred to as the first surface 400b, and a surface on the bonded to the lower surface of the solution holding container 22 on the opposite side is referred to as the second surface 400a.

Thus, the first surface 400b is coated with a solution containing the precursor of the photosensitive resin G having a polarity different from that of the photosensitive resin film 450 in FIG. 11 by spin coating, and thermal polymerization is performed by baking so as to remove the solvent. Exposure and development are performed on the photosensitive resin G so as to pattern the shape of the flow path 451.

Next, the photosensitive resin G patterned in a shape of the flow path 451 is coated from above with the solution containing the precursor of the photosensitive resin film 450 by spin coating, and thermal polymerization is performed by baking so as to remove the solvent. The photosensitive resin G and the photosensitive resin film 450 are not compatible since both of these have different polarities. Exposure and development are performed on the photosensitive resin film 450 so as to form the nozzle 110.

Subsequently, the inlet 411 for the solution is formed from the second surface 400a side of the silicon wafer 401 by anisotropic etching which uses a tetra methyl ammonium hydroxide (TMAH) solution and which utilizes a difference in an etching rate depending on a silicon crystal orientation. The inlet 411 for the solution opens at an angle of 54.7° with respect to the surface of the second surface 400a.

Next, the flow path 451 is formed by dissolving the photosensitive resin G with a solvent. Thereafter, a plurality of the droplet ejecting arrays 28 are separated and formed by dicing the disc-shaped silicon wafer 401. The second surface 400a of the silicon wafer 401 of the droplet ejecting array 28 is bonded to the bottom surface, on the same side as the opening 22a side surface, of the solution holding container 22.

Next, an operation according to the second embodiment will be described. The lower surface opening 22a on the bottom portion of the solution holding container 22 communicates with the inlet 411 and the flow path 451 of the droplet ejecting array 28. From the lower surface opening 22a of the bottom surface of the solution holding container 22, the solution held in the solution holding container 22 fills each pressure chamber 410 in the flow path 451 formed in the photosensitive resin film 450 via the inlet 411 formed in the silicon board 400.

In this position, if a voltage control signal is applied to the thin film heater 430, the heat energy generated from the thin film heater 430 heats and boils the solution contained in the pressure chamber 410. In this manner, the solution is ejected from the nozzle 110 as a solution droplet. A predetermined amount of fluid is dropped from the nozzle 110 into the two well openings 300 of the microplate 4.

In the first embodiment, the distance L1 between the adjacent nozzles 110 within nozzle group 173 (alternatively 171 or 172) is 0.25 mm. In the second embodiment, the distance L11 between the adjacent nozzles 110 within nozzle group 174 or 175 is 0.07 mm. Accordingly, the second embodiment enables the nozzles 110 to be arranged at a higher density. Therefore, the number of the nozzles arranged in each nozzle group (174 or 175) is 18 according to the second embodiment, and thus, the second embodiment enables the nozzles to be arranged 1.5 times more densely compared to the first embodiment.

As a result, the amount of time required to drop the solution into all wells of the 1,536 well microplate 4 in the first embodiment and the second embodiment, is as follows. In the droplet ejecting apparatus 2 according to the first embodiment, one solution holding container 22 communicates with the three nozzle groups 171, 172, and 173, which collectively include 36 nozzles. The droplet ejecting apparatus 2 according to the first embodiment thus simultaneously drops solution into three well openings 300 (each well receiving droplets from 12 nozzles at once). In the droplet ejecting apparatus 2 according to the second embodiment, one solution holding container 22 communicates with the two nozzle groups 174 and 175, which collectively include 36 nozzles. The droplet ejecting apparatus 2 according to the second embodiment thus simultaneously drops the solution into two well openings 300 (each well receiving droplets from 18 nozzles at once). Therefore, the times required to dispense a fixed amount of the solution to all wells of the 1,536 well microplate 4 can be the same for the first embodiment and the second embodiment.

In this case, according to the second embodiment, the number of nozzles of each nozzle group is 1.5 times of that of the first embodiment. Accordingly, the size of the droplet ejecting array 28 according to the second embodiment can be smaller than that of the droplet ejecting array 27 according to the first embodiment. Therefore, the number of the droplet ejecting arrays 28 which can be formed in the silicon wafer 401 can be further increased in the second embodiment compared to the first embodiment. Therefore, the production cost of the droplet ejecting apparatus 2 can be reduced.

According to the droplet ejecting apparatus 2 of the second embodiment, similarly to the first embodiment, the solution holding container 22 communicates with a plurality of the nozzle groups. Accordingly, the solution can be simultaneously dropped into a plurality of the well openings 300. Therefore, the solution can be dropped into every well of the 1,536 well microplate 4 in a shorter period of time. Therefore, it is possible to provide the droplet ejecting apparatus which restrains the volatilization of the solution contained in the solution holding container 22.

The actuator using the thermal jet method according to the second embodiment is the thin film heater 430. The solution is ejected by heating and boiling the solution with heat energy generated from the thin film heater 430 and by using the pressure generated therein. Therefore, the solution comes in contact with the thin film heater 430 which is heated up to 300° C. or higher. Accordingly, it is preferable to eject only a highly heat-resistant solution which is not degraded even when the temperature reaches 300° C. or higher. Since the structure of the thermal jet method is simpler than that of the piezoelectric jet method, the actuator can be miniaturized. Therefore, compared to the piezoelectric jet method, the nozzles can be arranged at higher density.

In the example embodiments described above, the solution holding container 22 communicates with a plurality of the nozzle groups. Thus, the solution can be simultaneously dropped into a plurality of the well openings 300. Accordingly, the solution can be dropped into every well of the 1,536 well microplate 4 in a short period of time. Therefore, it is possible to limit the effect of volatilization of the solution contained in the solution holding container 22. In this manner, it is possible to provide the droplet ejecting apparatus in which the solution can be dropped in a short period of time before the concentration of the compound is changed due to volatilization of the solution contained in the solution holding container 22, when a compound dissolved in the highly volatile solution is being dropped into 1,536, 3,456, 6,144 well plates.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

For example, the drive element 130 serving as a drive unit has a circular shape. However, the shape of the drive unit is not limited to a circular shape. The shape of the drive unit may be a rhombus shape or an elliptical shape, for example. Similarly, the shape of the pressure chamber 210 is not limited to a circular shape, and may be a rhombus shape, an elliptical shape, or a rectangular shape.

In the example embodiments, the nozzle 110 is disposed at the center of the drive element 130. However, the position of the nozzle 110 is not particularly limited as long as the solution of the pressure chamber 210 can be ejected from the nozzle 110. For example, the nozzle 110 may be formed outside the drive element 130, that is, not within an overlapping region of the drive element 130. If the nozzle 110 is disposed outside the drive element 130, the nozzle 110 does not need to be patterned by penetrating a plurality of film materials of the drive element 130. Likewise, the plurality of film materials of the drive element 130 does not need an opening patterning process to be performed at the position corresponding to the nozzle 110. The nozzle 110 can be formed by simply patterning the diaphragm 120 and the protective film 150. Therefore, the patterning process may be facilitated.

What is claimed is:

1. A droplet ejecting apparatus, comprising:
a plurality of nozzle groups each including a plurality of nozzles;
a plurality of pressure chambers each configured to supply a solution to a corresponding nozzle of a nozzle group in the plurality of nozzle groups;
a plurality of actuators each configured to cause a pressure change in a corresponding pressure chamber in the plurality of pressure chambers to control an ejection of a droplet of the solution from the corresponding nozzle; and
a solution holding container having a solution inlet for receiving solution and a solution outlet, the solution holding container being configured to supply the solution to the plurality of nozzle groups via the plurality of pressure chambers.

2. The apparatus according to claim 1, wherein
a distance between two adjacent nozzles in each nozzle group is shorter than a distance between two adjacent nozzle groups.

3. The apparatus according to claim 1, wherein
each nozzle group is spaced from each other nozzle group such that each nozzle group can be positioned above a different well of a multiwell plate such that droplets ejected from each respective nozzle group are received by a respectively different well of the multiwell plate.

4. The apparatus according to claim 3, wherein
the plurality of actuators operate such that droplets of the solution are ejected simultaneously from the plurality of nozzle groups.

5. The apparatus according to claim 1, wherein
each of the plurality of actuators comprises a piezoelectric film that is configured to deform a pressure chamber in the plurality of pressure chambers and cause the solution to be ejected.

6. The apparatus according to claim 1, wherein
each of the plurality of actuators comprises a thin film heater that is configured to heat the solution in one pressure chamber in the plurality of pressure chambers and cause the solution to be ejected.

7. A solution dispenser, comprising:
a base on which a multiwell plate can be disposed;
a droplet ejecting apparatus having first surface side facing the base and a second surface side opposite the first surface side, the droplet ejecting apparatus including:
a plurality of nozzle groups on the first surface side, each nozzle group including a plurality of nozzles, each nozzle group being disposed so as be positioned above a well of the multiwell plate;

a plurality of pressure chambers, each configured to supply a solution to a corresponding nozzle of a nozzle group in the plurality of nozzle groups;

a plurality of actuators, each configured to cause a pressure change in a corresponding pressure chamber in the plurality of pressure chambers to control an ejection of a droplet of the solution from the corresponding nozzle; and a solution holding container having a solution inlet for receiving solution and a solution outlet on the second surface side, the solution holding container being configured to supply the solution to the plurality of nozzle groups via the plurality of pressure chambers; and a moving stage connected to the droplet ejecting apparatus and configured to move the droplet ejecting apparatus to position the plurality of nozzle groups above wells of the multiwell plate.

8. The solution dispenser according to claim 7, wherein the moving stage is configured to move in a two dimensional plane parallel to the base.

9. The solution dispenser according to claim 7, wherein a distance between adjacent nozzles within each nozzle group is shorter than a distance between adjacent nozzle groups in the plurality of nozzle groups.

10. The solution dispenser according to claim 7, wherein each nozzle group is spaced from each other nozzle group such that each nozzle group can be positioned above a different well of a multiwell plate such that droplets ejected from each respective nozzle group are received by a respectively different well of the multiwell plate.

11. The solution dispenser according to claim 10, wherein droplets of the solution are ejected simultaneously from each nozzle group in plurality of nozzle groups.

12. The solution dispenser according to claim 7, wherein each of the plurality of actuators comprises a piezoelectric film that is configured to deform one pressure chamber in the plurality of pressure chambers and cause the solution to be ejected.

13. The solution dispenser according to claim 7, wherein each of the plurality of actuators comprises a thin film heater that is configured to heat the solution in one pressure chamber in the plurality of pressure chambers and cause the solution to be ejected.

14. A droplet ejecting apparatus, comprising:

a plurality of nozzle groups each including a plurality of nozzles;

a plurality of actuators each configured to control an ejection of a droplet of the solution from a corresponding nozzle of a nozzle group in the plurality of nozzle groups; and a solution holding container having a solution inlet for receiving solution and a solution outlet, the solution holding container being configured to supply the solution to the plurality of nozzle groups, the plurality of nozzle groups ejecting droplets of the solution at a same time.

15. The apparatus according to claim 14, wherein the plurality of nozzles in each nozzle group are arranged in an array having a width dimension less than a width dimension of a single well in a 1,536 well multiwell plate.

16. The apparatus according to claim 14, wherein a distance between two adjacent nozzles in each group is shorter than a distance between two adjacent groups of nozzles.

17. The apparatus according to claim 14, wherein each nozzle group is spaced from each other nozzle group such that each nozzle group can be positioned above a different well of a multiwell plate such that droplets ejected from each respective nozzle group are received by a different well of the multiwell plate.

18. The apparatus according to claim 17, wherein droplets of the solution are ejected simultaneously from each nozzle group in the plurality of nozzle groups.

19. The apparatus according to claim 14, wherein each of the plurality of actuators comprises a piezoelectric film that is configured to cause the solution to be ejected from the corresponding nozzle.

20. The apparatus according to claim 14, wherein each of the plurality of actuators comprises a thin film heater that is configured to heat the solution in the vicinity of the corresponding nozzle and cause the solution to be ejected from the corresponding nozzle.

* * * * *